United States Patent [19]
Mawad

[11] Patent Number: 6,071,286
[45] Date of Patent: Jun. 6, 2000

[54] COMBINATION ANGIOPLASTY BALLOON/ STENT DEPLOYMENT DEVICE

[76] Inventor: Michel E. Mawad, 6434 Auden, Houston, Tex. 77005

[21] Appl. No.: 08/880,591

[22] Filed: Jun. 23, 1997

Related U.S. Application Data

[60] Provisional application No. 60/038,793, Feb. 19, 1997.
[51] Int. Cl.[7] ...................................................... A61F 11/00
[52] U.S. Cl. .............................. 606/108; 623/1; 606/194; 604/96
[58] Field of Search .......................... 604/96–104; 606/1, 606/159, 108, 191–200; 623/1, 11, 12

[56] References Cited

U.S. PATENT DOCUMENTS

| | | | |
|---|---|---|---|
| 5,290,295 | 3/1994 | Querals et al. | 606/108 |
| 5,456,694 | 10/1995 | Marin et al. | 606/198 |
| 5,634,928 | 6/1997 | Fischell et al. | 606/194 |

*Primary Examiner*—Glenn K. Dawson
*Attorney, Agent, or Firm*—Conley, Rose & Tayon, P.C.

[57] ABSTRACT

An apparatus for performing balloon angioplasty and stent deployment in a vessel having a narrowed portion, including: a stent deployment member having an inner core and a stent, the inner core having a first lumen therethrough and proximal and distal ends, with the stent being releasably supported on the inner core, and an angioplasty balloon having a sealable distal end and an open proximal end, the proximal end being sealed to the inner core such that the balloon can be inflated by the passage of a fluid through the first lumen. Also disclosed is a method for widening a narrowed portion of a vessel, including: providing a balloon adjacent a stent on a single catheter, introducing a balloon at the narrowed portion, inflating the balloon, deflating the balloon, advancing the balloon beyond the narrowed portion, deploying the stent, and withdrawing the deflated balloon through the deployed stent.

12 Claims, 1 Drawing Sheet

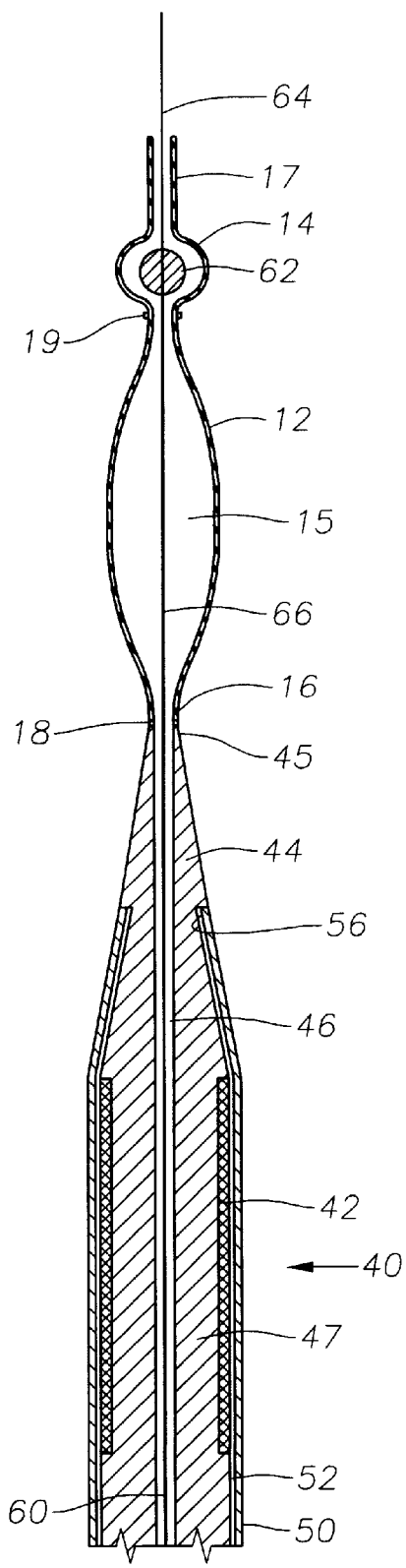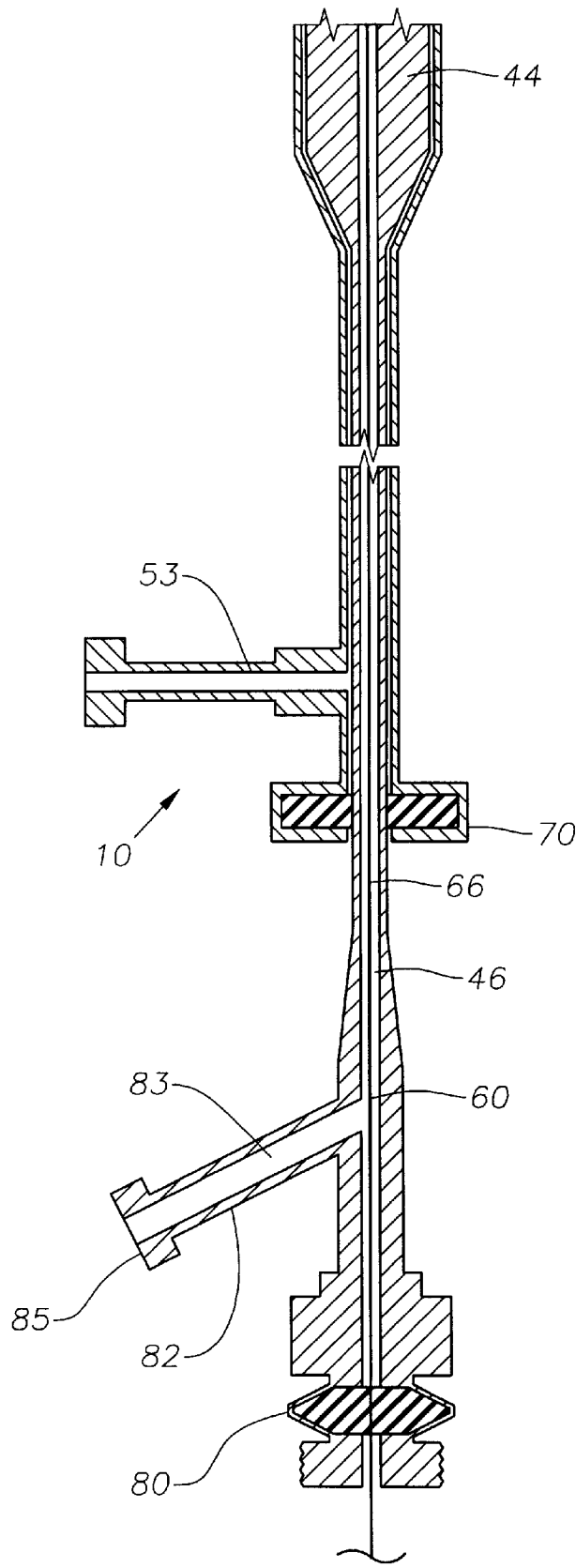
Fig. 1A
Fig. 1B

COMBINATION ANGIOPLASTY BALLOON/ STENT DEPLOYMENT DEVICE

The present application claims the benefit of 35 U.S.C. 111(b) provisional application Ser. No. 60/038,793, filed Feb. 19, 1997, and entitled Combination Angioplasty Balloon/Stent Deployment Device.

BACKGROUND OF THE INVENTION

Atherosclerotic disease of the carotid artery is almost exclusively located at the level of the common carotid bifurcation and often extends into the internal carotid artery. Atherosclerotic narrowing of the carotid artery often leads to stroke, which is one of the leading causes of death in North America and one of the major causes of long-term disability. Carotid Endarterectomy (CE) is the surgical procedure where the surgeon opens the diseased carotid artery and physically removes the plaque of atherosclerosis, thus reestablishing a normal caliber of the vessel and normal blood flow to the brain. There is early evidence, both in Europe and in North America, that balloon angioplasty of the carotid artery followed by carotid stenting can in fact open the narrowed and diseased artery. The role of the stent is to maintain long-term patency of the artery following angioplasty and to avoid long-term restenosis.

One of the major technical difficulties encountered in balloon angioplasty in the carotid circulation artery is the fact that the passage through the atherosclerotic artery is so small that area of stenosis often needs to be predilated with a small and low profile balloon in order to be able to position the stent delivery device and to deliver a self expandable stent at the desired location of the stenosis. The need to predilate the artery necessitates the passage of a low profile balloon through the area of stenosis, dilatation of the artery, and removal of the predilatation balloon, followed by passage of the stent deployment device through the same area of stenosis. This manipulation of the balloon and then the stent within the narrowed artery, which contains irregular and friable plaque, can cause thromboembolic complications. For example, dislodgment of a fragment of plaque can cause a stroke if it is not caught before it passes into the brain.

Hence, it is desirable to provide a device that requires minimal manipulation within the area of stenosis. It is further desired to provide a device that is capable of preventing any fragments of plaque that may become dislodged from passing up through the artery and into the brain.

SUMMARY OF THE INVENTION

The present invention is a combination balloon and stent that are mounted in series on a single catheter. The balloon is adjacent the remote end of the catheter and includes a valve mechanism adjacent its distal tip. The stent is a conventional stent that is contained prior to deployment between a sheath or sleeve and an inner core support. The proximal end of the balloon is sealed to the remote end of the core support, which has a lumen through which the guide wire passes and through which the balloon is inflated. The core support is slidable relative to the outer sheath such that movement of the core out of the sheath allows the stent to deploy.

The method of using the present invention comprises the steps of: inserting the balloon into the area of stenosis, inflating the balloon to pre-dilate the area, deflating the balloon to disengage it from the vessel wall, advancing the catheter so that the balloon moves beyond the area of stenosis, deploying the stent at the area of stenosis, and withdrawing the deflated balloon back through the deployed stent. In addition, the present method includes two optional steps. One entails re-inflating the balloon after advancing it to a point beyond the area of stenosis and before deploying the stent, so as to block off the vessel and prevent the passage of any potentially obstructive material. A second optional step entails re-inflating the balloon within the deployed stent prior to withdrawing the balloon so as to increase the deployed diameter of the stent.

The purpose of the present device is to perform both the predilatation angioplasty and the deployment of the self expandable stent using a single device, thereby obviating the need to change guidewires or catheters and thus reducing the incidence of thromboembolic complications.

BRIEF DESCRIPTION OF THE FIGURE

For a detailed description of a preferred embodiment of the invention, reference will now be made to FIG. 1, which is a schematic view of an angioplasty device constructed according to the present invention.

DETAILED DESCRIPTION OF A PREFERRED EMBODIMENT

As shown in FIG. 1, the present angioplasty device 10 comprises a low profile, single lumen predilatation balloon 12 mounted at the tip of a stent delivery device 40, which contains a constrained self expandable stent 42, so as to form a single catheter.

Stent delivery device 40 preferably comprises an inner core 44 having a lumen 46 therethrough and a reduced thickness portion 47, and an outer sheath 50. Inner core 44 and sheath 50 are preferably substantially coaxial, so that a small annular lumen 52 is formed between the inner wall of sheath 50 and the outer wall of inner core 44. An annular space is formed between reduced thickness portion 47 and the inner wall of sheath 50. A guidewire 60 extends from the proximal end of angioplasty device 10 through stent delivery device 40 via lumen 46. Guidewire 60 exits lumen 46 at the distal end of stent delivery device 40 and extends through balloon 12.

Guidewire 60 preferably comprises a tapered shaft 66 having a shapeable soft tip 64 at its distal end. Proximal shaft 66 of the guidewire is relatively stiff and preferably measures 32 to 35 thousandths of an inch in cross sectional diameter. The proximal stiffness of the guidewire allows for better handling and better tracking of the delivery sheath over the wire. In contrast, tip 64 is relatively flexible and is preferably 14–16 thousandths of an inch in cross sectional diameter. A preferred tip is made of a wound coil of gold or platinum wire. The soft tip 64 allows device 10 to cross the stenotic lesion in an atraumatic fashion and avoids irritation or injury of the distal segment of the vessel. This is particularly advantageous when the subject vessel includes the internal carotid artery at the base of the skull. Guidewire 60 includes an occlusion ball 62 located near its distal end and tip 64 forms the distal end of guidewire 60 beyond ball 62. The entire guidewire is preferably hydrophillically coated to facilitate catheterization of the artery and better tracking of the device.

Outer sheath 50 terminates proximally at a conventional hemostatic valve 70 that forms a seal with the outside of inner core 44. Between valve 70 and the wider portion of sheath 50 a side port 53 is preferably included for providing fluid access to lumen 52. The entire inner core 44 on which stent 42 is constrained moves both forward and backwards within the outer layer of sheath 50 through hemostatic valve 70. Moving inner core 44 forward removes stent 42 from annular lumen 52 and allows for the deployment of the stent; whereas moving inner core 44 backwards locks stent 42 against outer sheath 50 and aborts its deployment.

Similarly, inner core 44 terminates proximally at a rotating hemostatic valve 80. Rotating hemostatic valve 80 allows guidewire 60 to be advanced and controlled through the inner lumen 46. A side arm 82 includes a luer lock female adapter 85 and a bore 83 that communicates with inner lumen 46 and allows for continuous flush of heparinized solution around the hydrophilic guidewire.

Prior to deployment, stent 42 is housed in annular lumen 52. Stent 42 preferably comprises stainless steel, Nitinol or any other alloy that has a preshapable memory and a hoop strength capable of maintaining the diameter of the dilated artery. Stent 42 is preferably constructed so as to be self-expandable, either by means of a mechanical bias toward a larger diameter or by means of a triggering effect, such as an elevation in temperature, such as are used with memory metals. In a preferred embodiment, the expanded diameter of the stent can vary from 2 mm to 10 mm and its length can vary from 0.5 cm to 6 cm.

Stent 42 is preloaded in a constrained state in the annular space between narrowed portion 47 of inner core 44 and outer sheath 50 during manufacture or assembly of device 10. Sheath 50 holds the stent in its constrained state around inner core 44 and prevents it from expanding prematurely.

Balloon 12 preferably comprises a low profile single lumen balloon having an inflatable chamber 15, a distal open end 17 and an open proximal end 16 that is bonded and permanently mounted on distal end 45 of inner core 44. Balloon 12 is a conventional low-profile balloon, such as are known in the art, and can be inflated with a manual inflator. Balloon 12 is preferably capable of withstanding inflation pressures of up to 15 atmospheres. Balloon 12 preferably includes a ball catch chamber 14 between its distal end 17 and chamber 15. Occlusion ball 62 on guidewire 60 cooperates with ball catch chamber 14 to form a valve mechanism that seals balloon 12 and lumen 46. Pushing the guidewire 60 forward causes ball 62 to seat on the opening at the distal end of chamber 14, sealing it. Correspondingly, pulling the guidewire back disengages occlusion ball 62 from chamber 14 and allows for rapid deflation of the balloon as the inflating fluid exits the distal end of balloon 12. It will be understood that balloon 12 can be inflated and deflated by other techniques, including eliminating the ball valve, providing a balloon having a closed end and allowing the fluid to enter and exit the balloon volume via lumen 46. Balloon 12 preferably includes a proximal radiopaque marker 18 and a distal radiopaque marker 19 that can be used to determine its length during operation of the device.

In operation, the fully assembled device 10 as shown in the FIGURE is inserted in a conventional manner into a vessel and advanced through the lumen of the vessel until its tip crosses the stenotic region. The device is then advanced further, until the inflatable chamber 15 of balloon 12 is positioned within the stenotic region. Guidewire 60 is then advanced relative to inner core 44 until occlusion ball 62 closes the distal opening of chamber 14. Fluid is then pumped through bore 83 and lumen 46 into balloon 12, inflating balloon 12 so as to predilate the stenotic lesion. Once the predilatation is complete, guidewire 60 is retracted slightly relative to inner core 44 such that it disengages from chamber 14 and allows fluid from chamber 15 to flow out through end 17, thereby deflating balloon 12. The device 10 is then advanced farther into the vessel, until the balloon 12 is beyond the stenotic region. Stent delivery device 40 is then used to deploy the stent by moving inner core 44 and stent 42 forward with respect to sheath 50. This causes stent 42 to exit from annular lumen 52 through opening 56 in the distal end of sheath 50. Stent 42 then expands spontaneously due to inherent bias, or is triggered to expend through any various triggering techniques, including the application of heat or electric current thereto. In a preferred embodiment, annular lumen 52 is primed with heparinized normal saline solution through side port 53 prior to the deployment of the stent.

Once the stent is in place and expanded so as to engage the vessel wall, the catheter can be removed from the vessel by retracting the deflated balloon back through the expanded stent. Alternatively, balloon can be re-inflated, using the technique described above to achieve one or both of two additional steps. First, balloon 12 can be re-inflated after it has been advanced beyond the stenotic region. This serves the purpose of occluding the vessel during placement of the stent, so as to reduce the possibility of a fragment of plaque or the like breaking loose and escaping into the vessel system. Second, balloon 12 can be partially retracted re-inflated within stent 42 after stent 42 has been deployed. This serves the purpose of expanding stent 42 to a somewhat greater diameter than it might otherwise expand itself.

It will be recognized that various modifications can be made in the design and operation of the present invention without departing from the spirit thereof. Thus, while the principal preferred construction and mode of operation of the invention have been explained in what is now considered to represent its best embodiments, it should be understood that within the scope of the appended claims the invention may be practiced otherwise than as specifically illustrated and described.

What is claimed is:

1. An apparatus for performing balloon angioplasty and stent deployment in a vessel having a narrowed portion, comprising:

a stent deployment member comprising an inner core and a stent, said inner core having a first lumen therethrough and having a proximal end and a distal end and, said stent being releasably supported on said distal end of said inner core;

an outer sheath surrounding said inner core and said stent said outer sheath and said inner core defining an annular lumen therebetween, said stent being housed in said annular lumen and said outer sheath including a port for providing fluid access to said annular lumen;

an angioplasty balloon, said balloon having a sealable distal end and an open proximal end, said proximal end being affixed to said inner core such that said balloon can be inflated by the passage of a fluid through said first lumen; and a guide wire housed in said first lumen and extending to said distal end of said balloon, said guide wire including a valve mechanism for controlling inflation of said balloon.

2. The apparatus according to claim 1 wherein said valve mechanism is activated by said guide wire.

3. The apparatus according to claim 1 wherein said outer sheath is slidable with respect to said inner core.

4. The apparatus according to claim 1 wherein said stent is constrained in a first configuration by said outer sheath and assumes a second configuration when released from said annular lumen by relative sliding of said outer sheath and said inner core.

5. The apparatus according to claim 1 wherein said inner core includes a port for providing fluid access to said first lumen.

6. A method for widening a narrowed portion of a vessel, comprising:

(a) providing a single catheter having an inner lumen;

(b) providing a balloon and a stent on said catheter, said balloon having a proximal end adjacent to said stent and an open, sealable distal end;

(c) providing a sheath surrounding the stent, such that an annular lumen is defined between the catheter and the sheath;

(d) providing a port at the proximal end of the catheter, said port being in fluid communication with the annular lumen;

(e) introducing the balloon at the narrowed portion;

(f) sealing the distal balloon end and inflating the balloon;

(g) opening the distal balloon end and deflating the balloon;

(h) advancing the balloon beyond the narrowed portion;

(i) deploying the stent; and (j) withdrawing the deflated balloon through the deployed stent.

7. The method according to claim 6, further including the step of inflating the balloon between steps (h) and (i).

8. The method according to claim 6, further including the step of partially withdrawing the balloon and inflating the balloon inside of the deployed stent between steps (i) and (j).

9. An apparatus for performing balloon angioplasty and stent deployment in a vessel having a narrowed portion, comprising:

a stent deployment member comprising an inner core, an outer sheath and a stent, said inner core having a first lumen therethrough and having a proximal end and a distal end and, said inner core including a guide wire housed in said first lumen, and said outer sheath surrounding said inner core and defining an annular lumen therewith, said sheath including a port for providing fluid access to said annular lumen and being slidable with respect to said inner core, said stent being releasably supported on said distal end of said inner core in said annular lumen; and an angioplasty balloon, said balloon having a distal end and an open proximal end, said proximal end being affixed to the distal end of said inner core such that said balloon can be inflated by the passage of a fluid through said first lumen;

wherein said guide wire extends to said distal end of said balloon and includes a valve mechanism for controlling inflation of said balloon.

10. The apparatus according to claim 9 wherein said valve mechanism is activated by said guide wire.

11. The apparatus according to claim 9 wherein said stent is constrained in a first configuration by said outer sheath and assumes a second configuration when released from said annular lumen by relative sliding of said outer sheath and said inner core.

12. The apparatus according to claim 9 wherein said inner core includes a port for providing fluid access to said first lumen.

* * * * *